United States Patent [19]
Conlon, III et al.

[11] Patent Number: 5,122,459
[45] Date of Patent: Jun. 16, 1992

[54] GENE ENCODING BIOLOGICALLY ACTIVE HUMAN INTERLEUKIN 1

[75] Inventors: Paul J. Conlon, III; David J. Cosman; Kenneth H. Grabstein; Thomas P. Hopp; Shirley R. Kronheim; Alf D. Larsen; Carl J. March; Virginia L. Price; Douglas P. Cerretti, all of Seattle, Wash.

[73] Assignee: Immunex Corporation, Seattle, Wash.

[21] Appl. No.: 443,399

[22] Filed: Nov. 30, 1989

Related U.S. Application Data

[63] Continuation of Ser. No. 687,646, Dec. 31, 1984, abandoned.

[51] Int. Cl.$^5$ ............... C12P 21/02; C12P 19/34; C12N 15/00; C12N 1/16
[52] U.S. Cl. .................. 435/69.52; 435/69.1; 435/91; 435/172.3; 435/320.1; 435/255; 435/256; 536/27; 530/350; 935/13; 935/28; 935/37; 935/56; 935/61; 935/69
[58] Field of Search .......... 435/69.1, 69.52, 91, 435/172.3, 235.1, 240.1, 255, 252.33, 320.1, 256, 252.3; 536/27; 530/350; 935/10, 27, 31, 32, 34, 35, 56, 57, 58, 62, 70, 72, 81

[56] References Cited

U.S. PATENT DOCUMENTS

| | | | |
|---|---|---|---|
| 4,406,830 | 9/1983 | Fabricius et al. | 530/380 |
| 4,508,833 | 4/1985 | Sonneborn et al. | 530/351 |
| 4,762,914 | 8/1988 | Auron et al. | 530/351 |
| 4,766,069 | 8/1988 | Auron et al. | 435/70 |
| 5,001,057 | 3/1991 | Auron et al. | 935/69.52 |

FOREIGN PATENT DOCUMENTS 0092163  10/1983  European Pat. Off.
2063882   6/1981  United Kingdom.

OTHER PUBLICATIONS

Roberts et al. (1979) PNAS 76: 760–64.
Windle et al. (1984) J. Immunology 132: 1317–23.
Okayama et al. (1983) Molecular and Cellular Biol. 3: 280–89.
Lachman et al. (1983) FED Proc. vol. 42 pp. 2637–2645.
Clark et al (1984) Proc Nat'l Acad. Sci. USA vol. 81 pp. 2543–2547.
Suggs et al. (1981) Proc. Nat'l Acad. Sci. USA vol. 78 pp. 6613–6617.
Interview with European Patent Office Jun. 13, 1990.
Communication Pursant to Article 96(2) and Rule 51(2) EPC.
Dinarello et al., Proc. Nat'l. Acad. Sci. U.S.A. 74: 4624–27 (1977).
Scala et al., Nature 309: 56–59 (1984).
Letter of Dr. J. Oppenheim dated Sep. 21, 1990.
Auron et al., J. Mol. Cell. Immunol. 2: 169–177 (1985).
Dinarello et al., Rev. Inf. Diseases 6: 51–95 (1984).
Schmidt, J. Exp. Med. 160: 772–87 (1984).
Blyden et al., "Purification and Properties of Human Lymphocyte Activating Factor (LAF)", 118 J. Immunol. 1631–1638 (1977).

(List continued on next page.)

Primary Examiner—Joan Ellis
Attorney, Agent, or Firm—Foley & Lardner

[57] ABSTRACT

Double-stranded cDNA is prepared from polyadenylated RNA extracted from activated human peripheral blood adherent mononuclear cells. The cDNA is inserted within a plasmid vector and then the recombinant plasmid employed to transform an appropriate host. Transformed hosts are identified and grouped into pools. Plasmid DNA prepared from these pools is hybridized with a labeled, synthetic oligonucleotide probe corresponding to a portion of the amino acid sequence of the interleukin 1 protein. Pools of host cells that provide a positive signal to the probe are identified, plated out and then employed in direct bacterial colony hybridization with the same probe, thereby to isolate the particular positive colony. Plasmid DNA is prepared from this colony and characterized by restriction enzyme mapping and sequencing by chain-termination method. The coding region for the IL-1 gene is inserted into a shuttle vector for amplification of the vector followed by expression of functional IL-1.

11 Claims, 4 Drawing Sheets

OTHER PUBLICATIONS

Lachman et al., "Partial Purification of Human Lymphocyte-Activating Factor (LAF) by Ultra-filtration and Electrophoretic Techniques", 119 *J. Immunol.* 2019-2033 (1977).

Togawa et al., "Characterization of Lymphocyte-Activating Factor (LAF) Produced by Human Mononuclear Cells: Biochemical Relationship of . . . ", 122 *J. Immunol.* 2112-2118 (1979).

Mizel et al., "Characterization of Lymphocyte-Activating Factor (LAF) Produced by a Macrophage Cell Line, P338D$_1$; All . . . ", 120 *J. Immunol.* 1504-1508 (1978).

Mizel, "Physiochemical Characterization of Lymphocyte-Activating Factor (LAF)", 122 *J. Immunol.* 2167-2172 (1979).

Mizel et al., "Purification to Apparent Homogeneity of Murine Interleukin Id", 126 *J. Immunol.* 834-837 (1981).

Lomedico et al., "Cloning and Expression of Murine Interleukin-1 cDNA in *Escherichia coli*", 312 *Nature* 458-464 (1984).

Editorial, "Minisymposium on Regulation of Connective Tissue Cells by Immune and Inflammatory Cells", 1 *Lymphokine Res.* 53 (1982).

Welte et al., "Purification of Human Interleukin 2 to Apparent Homogeneity and its Molecular Heterogeneity", 156 *J. Exp. Med.* 454-464 (1982).

Acuto et al., "An Efficient Method for Purification of Human T-Cell Growth Factor", 53 *J. Immunol. Meth.* 15-26 (1982).

Oppenheim et al., "Interleukin 1 is More Than an Interleukin", *T-Lymphocytes Today* 89-95 (1983).

Kock et al., "Purification of Human Interleukin 1 by High-Performance Liquid Chromatography", 296 *J. Chromat.* 292-300 (1984).

Hanahan, "Studies of Transformation of *Escherichia coli* with Plasmids", 166 *J. Mol. Biol.* 557 (1983).

Stern et al., "Purification to Homogeneity and Partial Characterization of Interleukin 2 from Human T-cell Leukemia", *Proc. Nat'l. Acad. Sci. USA* 871-875 (1984).

Beggs, "Transformation of yeast by a replicating hybrid plasmid", *Nature* (London) 104-108 (1974).

March et al., "Cloning, sequence and expression of two distinct human interleukin-1 complementary DNAs", *Nature* 315:641-647 (1985).

G. Di Sabato, "Purification and initial characterization of rat interleukin 2", 79 *Proc. Natl. Acad. Sci USA* 3020-3023 (1982).

Mosley, et al. *Proc. Nat'l Acad. Sci.* (USA) 84:45,72, 4576 (1987).

Devereux et al., *Nucleic Acid Research*, 12: 387-95 (1984).

Andrew C. Webb, et al. "Molecular Organization and Expression of the Prointerleukin-1β Gene" in Recombinant Lymphokines and Their Receptors, (1987), pp. 139-158.

PARTIAL RESTRICTION MAP OF PLASMID IL-1 X-14 IN THE REGION OF THE IL-1 GENE

FIG. 2A

```
5'-T TTT CGA GGC AAA AGG CAA AGG CTG CTC TGG GAT TCT CTT CAG  46
     Phe Arg Gly Lys Arg Gln Lys Arg Leu Leu Trp Asp Ser Leu Gln

CCA ATC TTC AAT GCT CAA GTG TCT GAA GCA GCC ATG GCA GAA GTA  91
   Pro Ile Phe Asn Ala Gln Val Ser Glu Ala Ala Met Ala Glu Val

CCT AAG CTC GCC AGT GAA ATG ATG GCT TAT AGT GGC AAT GAG     136
   Pro Lys Leu Ala Ser Glu Met Met Ala Tyr Ser Gly Asn Glu

GAT GAC TTG TTT GAA GCT GAT GGC CCT AAA CAG ATG AAG TGC     181
   Asp Asp Leu Phe Glu Ala Asp Gly Pro Lys Gln Met Lys Cys

TCC TTC CAG GAC CTG CTC TGC CCT CTG GAT GGC GGC ATC CAG     226
   Ser Phe Gln Asp Leu Leu Cys Pro Leu Asp Gly Gly Ile Gln

CTA CGA ATC TCC GAC CAC CAC TAC AGC AAG TTC AGG CAG GCC     271
   Leu Arg Ile Ser Asp His His Tyr Ser Lys Phe Arg Gln Ala

GCG TCA GTT GTT GTG GCC ATG GAC AAG CTG AGG ATG CTG GTT     316
   Ala Ser Val Val Val Ala Met Asp Lys Leu Arg Met Leu Val

CCC TGC CCA CAG ACC TTC GAG AAT GAC CTG AGC ACC TTC TTT     361
   Pro Cys Pro Gln Thr Phe Glu Asn Asp Leu Ser Thr Phe Phe

CCC TTC ATC TTT GAA GAA GAG CCT ATC TTT GAC ACA TGG GAT     406
   Pro Phe Ile Phe Glu Glu Glu Pro Ile Phe Asp Thr Trp Asp

AAC GAG GCT TAT GTG CAC GAT GCA CCT GTA CGA TCA CTG AAC TGC 451
   Asn Glu Ala Tyr Val His Asp Ala Pro Val Arg Ser Leu Asn Cys  8
                                        Hind III
   ACG CTC CGG GAC TCA CAG CAA AAA AGC TTG GTG ATG TCT GGT CCA 496
   Thr Leu Arg Asp Ser Gln Gln Lys Ser Leu Val Met Ser Gly Pro 23
        Hpa II
```

FIG. 2B

```
     Nde I
    1 TAT GAA CTG AAA GCT CTC CAC CTC CAG GGA CAG GAT ATG GAG CAA 541
      Tyr Glu Leu Lys Ala Leu His Leu Gln Gly Gln Asp Met Glu Gln 38

CAA GTG GTG TTC TCC ATG TCC TTT GTA CAA GAA GGA GAA AGT AAT 586
      Gln Val Val Phe Ser Met Ser Phe Val Gln Glu Gly Glu Ser Asn 53

GAC AAA ATA CCT GTG GCC TTG GGC CTC AAG GAA AAG CTG TAC 631
      Asp Lys Ile Pro Val Ala Leu Gly Leu Lys Glu Lys Asn Leu Tyr 68
                                                      Pvu II
      CTG TCC TGC GTG TTG AAA GAT GAT AAG CCC ACT CTA CAG CTG GAG 676
      Leu Ser Cys Val Leu Lys Asp Asp Lys Pro Thr Leu Gln Leu Glu 83

AGT GTA GAT CCC AAA AAT TAC CCA AAG AAG ATG AAG AAG CGA 721
      Ser Val Asp Pro Lys Asn Tyr Pro Lys Lys Met Lys Lys Arg 98

TTT GTC TTC AAG ATA GAA ATC AAT AAC AAG CTG GAA TTT GAG 766
      Phe Val Phe Lys Ile Glu Ile Asn Asn Lys Leu Glu Phe Glu 113

TCT GCC CAG TTC CCC AAC TGG TAC ATC AGC ACC TCT CAA GCA GAA 811
      Ser Ala Gln Phe Pro Asn Trp Tyr Ile Ser Thr Ser Gln Ala Glu 128
                                                         Serf I
      AAC ATG CCC GTC TTC CTG GGA GGG ACC AAA GGC GGC GAT ATA 856
      Asn Met Pro Val Phe Leu Gly Gly Thr Lys Gly Gly Asp Ile 143

ACT GAC TTC ACC ATG CAA TTT GTG TCT TCC TAA AGAGAGCTGTAC 901
      Thr Asp Phe Thr Met Gln Phe Val Ser Ser End              153

CCAGAGAGTCCTGTGCTGAATGTGGACTCAATCCCCTAGGGCTGGC           946

AGAAAGGGAACAGAAAGGTTTTTGAGTACGGCTATAGCCCTGGACT          991

TTCCTGTTGTCTACACCAATGCCCAACTGCCTGCCTTAGGGTAGT          1036

GCTAAGAGAGGATCTCCTGTCCATCAGCCAGGACAGTCAGCTCTCTC        1081

CTTTCAGGGCCAATCCCAGCCCTTTGTTGAGCCAGGCCCTCTCT - 3'      1125
```

GENE ENCODING BIOLOGICALLY ACTIVE HUMAN INTERLEUKIN 1

This application is a continuation of application Ser. No. 06/687,646, filed Dec. 31, 1984, now abandoned.

TECHNICAL FIELD

The present invention relates to interleukin 1 (hereinafter "IL-1"), and more particularly to the cloning of a gene for human IL-1 by use of a synthetic oligonucleotide probe derived from the amino acid sequence of purified IL-1, to screen a complementary deoxyribonucleic acid ("cDNA") library synthesized from IL-1 messenger ribonucleic acid ("mRNA"); and, the characterization of the screened IL-1 gene.

BACKGROUND OF THE INVENTION

IL-1, formerly known in the literature as "lymphocyte activating factor" or "LAF," is a hormone secreted by macrophages while undergoing on immune response. This protein factor regulates a wide range of immunological and non-immunological responses. For instance, it is considered that IL-1 mediates activities referred to as endogenous or leukocytic pyrogen, B-cell activating factor (BAF), epidermal cell thymocyte activating factor (ETAF), leukocyte endogenous mediator (LEM), bone resorption factor active in rheumatoid arthritis, and a variety of other activities.

Although researchers have identified many of the biological properties of IL-1, the chemical nature of this hormone is not well understood. To date, this has been hampered, at least in part, by the unavailability of sufficient quantities of IL-1 in purified form to carry out necessary investigations.

Attempts have been made in the past to purify and partially characterize IL-1 derived from both human and murine sources. For instance, Mizel, 122 *J. Immunol.* 2167–2172 (1979), reported the production of murine IL-1 from the macrophage cell line, $P388D_1$, cultured in a supplemented growth medium together with phorbol myristic acetate as an activating agent. The IL-1 from the culture fluid was subjected to ammonium sulfate precipitation, diethyl amino ethyl ("DEAE") cellulose column chromatography, ultrafiltration and Sephacryl S200 column chromatography. The resulting active fractions were analyzed by sodium dodecyl sulfate ("SDS")-polyacrylamide gel electrophoresis ("PAGE") and were found to have a molecular weight in the range of 12,000 to 16,000 daltons. Through isoelectrofocusing ("IEF") in polyacrylamide gels, the pI of the IL-1 was found to be in the range of from 5.0 to 5.4.

In a subsequent communication Mizel et al., 126 *J. Immunol.* 834–837 (1981), discussed purifying IL-1 from the same $P388D_1$ cell line as used in Mizel, supra, to "apparent homogeneity" by ammonium sulfate precipitation, phenyl Sepharose chromatography, Ultrogel AcA54 gel filtration chromatography and preparative flat-bed IEF. From the IEF, the pI of the IL-1 was measured to be about 4.9 to 5.1. Through gel electrophoresis the molecular weight of the IL-1 molecule was determined to be approximately 14,000 daltons.

Researchers have also investigated IL-1 produced from human peripheral blood leukocytes and monocytes. Blyden et al., 118 *J. Immunol.* 1631–1638 (1977), disclosed a protocol for concentrating IL-1 prepared from human peripheral blood leukocytes by Sephadex G-100 column chromatography. This procedure was reported to result in a four-to-five fold concentration of the crude IL-1. DEAE-Bio-Gel A anion exchange chromatography was employed to remove the albumin from the serum used during the preparation of the crude IL-1. Next, the collected active fractions were adsorbed onto a hydroxylapatite column. Fractions containing peak IL-1 activity were then applied to a CM-Bio-Gel A cationic exchange resin. By these procedures, about 20% of the initial IL-1 was recovered. The resulting IL-1 was found to have a molecular weight of about 13,000 daltons and a pI of approximately 6.8 to 7.2.

Crude IL-1 prepared from human leukocytes by Togawa et al., 122 *J. Immunol.* 2112–2118 (1979) was initially processed by membrane filtration and then applied to a Bio-Gel P-100 chromatography column which disclosed two major peaks of activity, one in the range of from 12,000 to 22,000 daltons and another in the range of bout 50,000 to 70,000 daltons. Active fractions in the lower molecular weight region of the Bio-Gel P-100 column were pooled, applied to a Blue Sepharose column, and then applied to a DEAE-cellulose ion-exchange chromatography column. Thereafter, the IL-1 containing fractions were pooled and applied to a hydroxylapatite chromatography column. Togawa et al. discovered that when the lower molecular weight IL-1 activity resulting from each of these procedures was reconstituted with 2% human serum, concentrated and rechromatographed on Bio-Gel P-100, a significant portion of the higher molecular wight activity appeared.

In a more recent study, Lachman, 42 *Federation Proceedings* 2639–2645 (1983), reported preparing IL-1 by culturing peripheral blood monocytes or leukemic cells obtained from acute monocytic leukemia or acute myelomonocytic leukemia patients in a serum supplemented culture medium together with lipopolysaccharide ("LPS") to stimulate IL-1 production. Hollow fiber diafiltration and ultrafiltration were used to separate a lower molecular weight activity from most of the serum proteins. This lower weight activity was subjected to IEF in an Ampholine and sucrose gradient. From this procedure, the IL-1 activity was found to have a pI of about 6.8 to 7.2. The isoelectrofocused IL-1 activity was then subjected to SDS-PAGE which indicated that the human IL-1 being analyzed had a molecular weight of about 11,000 daltons. Lachman reported that the overall recovery of IL-1 activity from the above procedures was poor, in the range of about 4%.

Applicants have purified IL-1 to homogeneity using a combination of ion-exchange chromatographic procedures together with dye-ligand binding chromatography. Use of these procedures resulted in elaboration of a 17,500 dalton protein containing IL-1 activity. By trypsin degradation of the purified IL-1 protein, IL-1 peptides were liberated, one of which was subjected to amino acid sequence determination. Although applicants have been successful in purifying IL-1, the techniques developed for such purification remain costly and time consuming.

The availability of adequate quantities of homogeneous human IL-1 could be valuable in investigations and possible treatment of autoimmune disorders such as arthritis and lupus erythematosis. Also, human IL-1 in greater purity and larger quantities than heretofore available, could prove useful in achieving successful wound and burn healing.

One potential method of providing relatively large quantities of homogeneous human IL-1 is through recombinant DNA techniques. Recombinant DNA techniques have been developed for economically producing a desired protein once the gene coding for the protein has been isolated and identified. A discussion of such recombinant DNA techniques for protein production is set forth in the editorial and supporting papers in Vol. 196 of *Science* (April, 1977). However, to take advantage of the recombinant DNA techniques discussed in this reference, the gene coding for human IL-1 must first be isolated.

SUMMARY OF THE INVENTION

In accordance with the present invention, a gene coding for human IL-1 was isolated from a cDNA library with a synthetic oligonucleotide probe corresponding to a portion of the amino acid sequence of human IL-1. Total human RNA was extracted from cells thought to produce relatively high levels of IL-1. Polyadenylated mRNA was isolated from the total RNA extract. A cDNA library was constructed by reverse transcription of size separated polyadenylated mRNA with reverse transcriptase. The DNA was rendered double-stranded with DNA polymerase I and inserted into an appropriate cloning vector. Resultant recombinant cloning vectors were used to transform an appropriate host.

Transformed hosts were identified and grouped into pools. Plasmid DNA prepared from these pools was hybridized with the oligonucleotide probe that had been radiolabeled. The pool(s) of clones that gave a positive signal to the probe was identified and then the putative pool subdivided and the hybridization screen repeated. By this procedure, a single transformant was eventually identified. Plasmid DNA was prepared from this transformant and characterized by restriction endonuclease digestion. The IL-1 gene was sequenced to establish its nucleotide and amino acid composition. Also the IL-1 gene was cloned in an *E. coli*/yeast cell system to express mature IL-1, and then biological assays were conducted to confirm that the expressed protein product is IL-1.

BRIEF DESCRIPTION OF THE DRAWINGS

The details of typical embodiments of the present invention will be described in connection with the accompanying drawings, in which:

FIGS. 2A and B illustrate the nucleotide sequence and the corresponding amino acid sequence of the IL-1 gene as contained in the nucleotide fragment in FIG. 1, with the nucleotides being numbered from the beginning of the sequence shown in FIG. 2A and the amino acids being numbered from the mature $NH_2$-terminus of the protein, i.e., the Ala residue denoted by a downward-pointing, vertical arrow in the figure, to the termination codon TAA at residue number 153; and, FIG. 3 illustrates the strategy employed to clone the coding region of the IL-1 gene in a shuttle vector used to transform yeast hosts to express functional IL-1.

DESCRIPTION OF THE INVENTION

Sources of Human IL-1 Producing Cells

Figure 1:
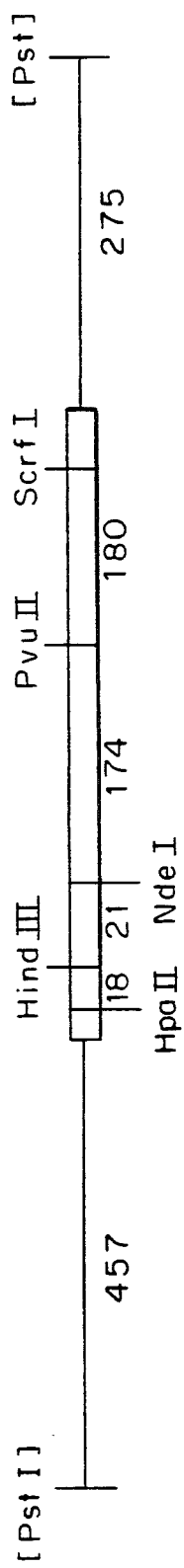
FIG. 1 illustrates a partial restriction mpa of the IL-1 gene.

Preferably, a cDNA library, from which genes coding for human IL-1 will be sought, is constructed from cells previously found to produce relatively high levels of other lymphokines, under the assumption that they might also produce human IL-1. These sources may include malignant cell lines, such as acute myelogenous leukemia cells.

Activated human peripheral blood adherent mononuclear cells also potentially may be a source of IL-1 molecules. For use in the present invention, the peripheral blood mononuclear cells can be separated from whole blood by standard techniques, such as by Ficoll-Hypaque centrifugation. Adherent cells are selected by plastic adherence and stimulated with *Escherichia coli* ("*e. coli*") LPS in vitro in a serum-containing medium.

Applicants found that stimulation of such adherent cells with *E. coli* LPS leads to elaboration of significant quantities of IL-1. As set forth infra, applicants have successfully isolated the IL-1 gene from a cDNA library prepared from LPS activated adherent leukocytes.

Preparation of RNA from Human IL-1 Producing Cells

Total RNA from human potentially IL-1-producing cells is extracted by standard methods, such as disclosed by Chirgwin et al., 18 *Biochemistry* 5294 (1979), and Maniatis et al., *Molecular Cloning, a Laboratory Manual*, Cold Spring Harbor Laboratory, Cold Spring Harbor, N.Y. (1982).

As is well known, when extracting RNA from cells, it is important to minimize ribonuclease ("RNase") activity during the initial stages of extraction. One manner in which this is accomplished is to denature the cellular protein, including the RNase, at a rate that exceeds the rate of RNA hydrolysis by RNase. In the procedures of Chirgwin et al., supra, and Maniatis et al., supra at 196, this is carried out by use of guanidinium thiocyanate, together with a reducing agent, such as 2-mercaptoethanol (to break up the protein disulfide bonds). The RNA is isolated from the protein by standard techniques, such as phenol/chloroform extraction, ethanol precipitation or sedimentation through cesium chloride.

Next, polyadenylated mRNA is separated from the extracted protein. Although several techniques have been developed to carry out this separation process, one preferred method is to chromatograph the polyadenylated mRNA on oligo (dT)-cellulose as described by Edmonds et al., 68 *Proc. Natl. Acad. Sci.* 1336 (1971); Aviv and Leder, 69 *Proc. Natl. Acad. Sci.* 1408 (1972); and, Maniatis et al., supra at 197. The oligo (dT)-cellulose column is prepared with a loading buffer and then the mRNA applied to the column. Thereafter, the column is initially washed with a buffer solution to remove the non-polyadenylated mRNA and then the polyadenylated mRNA is eluted from the column with a buffered, low ionic strength eluant. The integrity of the polyadenylated mRNA is verified by gel electrophoresis.

The polyadenylated mRNA is then sized by electrophoresis through methylmercury agarose and gel fractions corresponding to different size classes of mRNA are then translated in vitro, by use of standard rabbit reticulocyte lysates technique, such as described by: Palmiter, 248 *J. Biol. Chem.* 2095 (1973); Pelham and Jackson, 667 *Eur. J. Biochem.* 246 (1976); and, Lee et al., 253 *J. Biol. Chem.* 3494 (1978). Kits for the rabbit reticulocyte assay are commercially available from many sources, such as from Bethesda Research Laboratories, Gaithersburg, Md. Alternatively, the mRNA translation can be carried out by microinjection of the mRNA into frog Xenopus laevis ("X. laevis") oocytes using standard techniques, such as described by Stoma et al., 79 Meth. Enzym. 68 (1981). Fluids liberated by either reticulocyte lysate translations, or by mRNA microinjected oocytes are then tested for the presence of IL-1 activity. mRNA gel fractions which, when translated in vitro gave rise to IL-1 activity, are selected as a source of mRNA for cDNA construction.

In the X. laevis oocyte translation procedure, approximately 50 nanoliters ("nl") of mRNA (dissolved in sterile $H_2O$ at a concentration of 0.5–1 mg/ml) is injected into each oocyte. The oocytes are harvested from X. laevis (Nasco, Fort Atkinson, Wis.) and incubated in 150 ml of oocyte incubation medium (88 mM NaCl, 1 mM KCl, 2.4 mM $NaHCO_3$, 0.82 mM $MgSO_4$.7 $H_2O$, 0.33 mM Ca $(NO_3)_2$. $4H_2O$, 0.41 mM $CaCl_2$. $6H_2O$, 7.5 mM Tris base, 18 units/ml (11 ug/ml) penicillin G potassium, and 18 ug/ml streptomycin). The final pH of the medium is adjusted to 7.6 with HCl and then sterilized by filtration. After injection, the oocytes are placed in 0.1 ml of fresh oocyte incubation medium and incubated for 18 hours at 23° C. in a 1.5 ml sterile conical polypropylene tube. After incubation, the oocytes are homogenized manually in the same conical tube and then the resulting extract is centrifuged.

Thymocyte Proliferation Assay

As noted above, mRNA translations by the rabbit reticulocyte lysates or the X. laevis oocytes are assayed by testing for the presence of IL-1 activity in the fluids liberated by the lysates or the oocyate extract. A first assay involves ascertaining the capacity of a sample of the lysate or oocyte extract to induce proliferation of thymocytes derived from CD-1 mice. In this assay, approximately $1 \times 10^6$ thymocyte cells, obtained from 10 to 12 week old CD-1 mice (Charles River Breeding Laboratories, Wilmington, Md.), re seeded in round bottom microplate wells (Corning Plastics, Corning, N.Y.) in the presence of three-fold serial dilutions of the IL-1 containing fluid samples. The thymocytes are cultured in 150 microliters ("ul") of MEM containing 50 U/ml penicillin, 50 micrograms ("ug")/ml streptomycin, 2 millimolar ("mM") glutamine, 0.2 mM gentamycin, 10 mM HEPES buffer, ("Supplemented MEM"), pH 7.4, together with 3% v/v human serum and $10^{-5}$ M 2-mercaptoethanol. The samples are cultured for 72 hours at 37° C. in an atmosphere of 5% $CO_2$ in air. Thereafter the cultures are pulsed for approximately 4 hours with 0.5 microcuries ("uCi") of tritiated thymidine ("$^3$H-Tdr"), (New England Nuclear, Boston, Mass., 2 Ci/mM specific activity), after which the cultures are harvested onto glass fiber filter strips, for instance with the aid of a multiple-automated sample harvester. $^3$H-Tdr incorporation is then measured by liquid scintillation counting. Details of this procedure are set forth by Gillis et al., 120 J. Immunol. 2027 (1978) and in U.S. Pat. No. 4,411,992.

By this thymocyte proliferation assay procedure, only the CD-1 thymocytes cultured in the presence of IL-1 incorporate $^3$H-Tdr in a dose dependent manner. CD-1 cells cultured in the absence of IL-1 incorporate only background levels of $^3$H-Tdr. IL-1 activity is calculated from the linear portion of the $^3$H-Tdr incorporation data in a manner similar to the procedure used by Gillis et al. supra, for determining interleukin-2 activity. Units of IL-1 activity are determined as the reciprocal dilution of a sample which generates 50% of maximal thymocyte $^3$H-Tdr incorporation as compared to a laboratory standard. For example, if a sample generates 50% of maximal thymocyte $^3$H-Tdr incorporation at a dilution of 1:15, then one unit ("U") of IL-1 is found in 1/15 of the 150 ul assay volume or 10 ul is said to contain one U of activity. The total sample would, therefore, contain 100 U [1,000 (ul/ml)÷10 ul (per U)] of IL-1 activity/ml. See Gillis et al., supra.

IL-1 Conversion Assay

A second alternative assay for IL-1 activity may be employed which takes advantage of the fact that IL-1 was found by applicants to convert an interleukin 2 ("IL-2") nonproducer murine tumor cell line, LBRM-33-145, to an IL-2 producer. In this assay LBRM-33-aA5 cells, ATCC No. CRL-8079, are inactivated by addition of 50 ug/ml of mitomycin C and incubated for 1 hour at 37° C. 100 ul of the inactivated LBRM-33-1A5 cells ($5 \times 10^5$ cells/ml) are cultured in 96-well flat-bottomed plates in the presence of an equal volume of the mitogen, phytohemagglutinin ("PHA") (1% final concentration) together with serial dilutions of IL-1 containing fluid samples. At hourly time intervals the existence of IL-2 activity, generated by IL-1 triggered, mitomycin C - inhibited LBRM-33-1A5 cells (and thus IL-1 activity), is directly ascertained by adding 50 ul of IL-2 dependent CTLL-2 cells ($8 \times 10^4$ cells/ml). The microwell cultures are then incubated for 20 additional hours followed by a 4 hour pulse with 0.5 uCi of $^3$H-Tdr (New England Nuclear, Boston, Mass., 2 Ci/mM specific activity). Thereafter, the thymidine-pulsed cultures are harvested onto glass fiber filter strips with the aid of a multiple automated sample harvester (MASH II; Microbiological Associates, Bethesda, Md.). $^3$H-Tdr incorporation is measured by liquid scintillation counting. Details of this procedure are set forth in Gillis et al. supra, and in U.S. Pat. No. 4,411,992. In this assay, only the CTLL-2 cells cultured in the presence of IL-2 incorporate $^3$H-Tdr in a dose dependent manner. CTLL-2 cells cultured in the absence of IL-2 (and thus IL-1) incorporate only background levels of $^3$H-Tdr. This "conversion" assay has the advantage of being quicker (completion within 24 hours) and approximately 1000 to 10,000 times more sensitive than the above-discussed thymocyte proliferation assay. Nevertheless, both the "conversion" and "proliferation" assays may be employed in conjunction with the present invention.

Preparation of cDNA from mRNA

A library of double-stranded cDNA corresponding to the mRNA, as prepared and assayed above, is constructed by known techniques employing the enzyme reverse transcriptase. One such procedure which may be employed in conjunction with the present invention is detailed by Maniatis et al., supra at 230. Briefly, the polyadenylated mRNA is reverse transcribed by using oligo-dT, that has been hybridized to the polyadenylated tail of the mRNA, as a primer for a first cDNA strand. This results in a "hairpin" loop at the 3' end of the initial cDNA strand that serves as an integral primer for the second DNA strand. Next, the second cDNA strand is synthesized using the enzyme DNA polymerase I and the hairpin loop is cleaved by S1 nuclease to produce double-stranded cDNA molecules. The double-stranded cDNA is fractionated by any convenient means to remove the shorter strands, thereby avoiding the needles cloning of small cDNA fractions.

It is to be understood that in accordance with the present invention, alternative standard procedures may be employed to prepare double-stranded cDNA from mRNA. One such alternative technique is disclosed by Land et al., 9 *Nucl. Acids Res.* 2251 (1981). In the Land et al. protocol, the hairpin loop is not used as a primer for the second cDNA strand. Rather, the 3' end of the first cDNA strand is tailed with dCMP residues using terminal deoxynucleotidyl transferase ("TdT"). This produces a 3' tail of poly-C residues. Then the synthesis of the second strand is primed by oligo-dG hybridized to the 3' tail. This technique is said to help avoid losing portions of the 5' tail of the second cDNA strand which might occur if the hairpin is cleaved with S1 nuclease, as in the Maniatis et al. protocol.

Cloning of cDNA

Next, the double-stranded cDNA is inserted within a cloning vector which is used to transform compatible prokaryotic or eukaryotic host cells for replication of the vector. Thereafter, the transformants are identified and plasmid DNA prepared therefrom.

To carry out the present invention, various cloning vectors may be utilized. Although the preference is for a plasmid, the vector may be a bacteriophage or a cosmid. If cloning occurs in mammalian cells, viruses also can be used as vectors.

If a plasmid is employed, it may be obtained from a natural source or artificially synthesized. The particular plasmid chosen should be compatible with the contemplated transformation host, whether a bacteria such as *E. coli*, yeast or other unicellular microorganism. The plasmid should have the proper origin of replication for the particular host cell to be employed. Also, the plasmid should have a phenotypic property that will enable the transformed host cells to be readily identified and separated from cells that do not undergo transformation. Such phenotypic characteristics can include genes providing resistance to growth inhibiting substances, such as an antibiotic. Plasmids are commercially available that encode genes resistant to various antibiotics, including tetracycline, streptomycin, sulfa drugs, penicillin and ampicillin.

If *E. coli* is employed as the host cell, many possible cloning plasmids are commercially available which may be used in conjunction with the present invention. A preferred plasmid for performing the present invention is pBR322. This plasmid has ben fully sequenced, as set forth in Sutcliffe, 43 *Cold Spring Harbor Symp. Quant. Biol.* 77 (1979). A significant advantage of this plasmid is that it has 11 known unique restriction sites, including the Pst I site in the ampicillin resistant gene. This feature is particularly useful for cloning by the homopolymer tailing method.

If a bacteriophage is used instead of a plasmid, such phages should have substantially the same characteristics noted above for selection of plasmids. This includes the existence of a phenotypic marker and ligatable termini for attachment of foreign genes.

Preferably, in the present invention, the double-stranded cDNA, having blunt ends, is inserted into a plasmid vector by homopolymeric tailing. As is well known in the art, in this technique, complementary homopolymer tracks are added to the strands of the cDNA and to the plasmid DNA. The vector and double-stranded cDNA are then joined together by hydrogen bonding between complementary homopolymer tails to form open, circular hybrid molecules capable of transforming host cells, such as *E. coli*.

In one procedure for homopolymeric tailing, approximately 50 to 150 dA nucleotide residues are added to the 3' ends of linearized plasmid DNA. A similar number of dT nucleotide residues are added to the 3' ends of the double-stranded cDNA and then the cDNA and plasmid joined together.

In an alternative and preferred method, dG tails are added to the 3' ends of the cloning vector that has been cleaved with an appropriate restriction enzyme. For instance, if the pBR322 plasmid is employed, the restriction enzyme Pst I may be used to digest the plasmid at the ampicillin resistant gene. Complementary dC tails are added to the 3' ends of the double-stranded cDNA prior to insertion of the cDNA segment in the plasmid with an appropriate annealing buffer.

It is to be understood that the double-stranded cDNA may be inserted within plasmid cloning vectors by other various standard methods. One such alternative technique involves attaching synthesized nucleotide linkers to the ends of the cDNA strands by using DNA ligase. The linkers are cleaved with a restriction enzyme to generate cohesive termini for insertion within a plasmid cleaved with the same restriction enzyme. Scheller et al., 196 *Science* 177–180 (1977); Maniatus et al., supra at 219.

The recombinant DNA plasmids, as prepared above, are used to transform host cells. Although the host may be any appropriate prokaryotic or eukaryotic cell, it is preferably a well-defined bacteria, such as *E. coli* or a yeast strain. Such hosts ar readily transformed and capable of rapid growth in culture. Other forms of bacteria, such as salmonella or pneumococcus, may be substituted for *E. coli*. In place of bacteria, other unicellular microorganisms may be employed, for instance, fungi and algae. Whatever host is chosen, it should not contain a restriction enzyme that would cleave the recombinant plasmid.

If *E. coli* is employed as a host, preferable strains are MM294 and RR1. Protocols for transformation of the MM294 host by a plasmid vector are well known, as set forth in Maniatis et al., supra at 255; and, Hanahan, 166 *J. Mol. Biol.* 557 (1983). Protocols for transformation of the RR1 host by a plasmid vector are also well known as set forth in Bolivar et al., 2 *Gene* 95 (1977) and Peacock et al., 655 *Biochem. Biophys. Acta.* 243 (1981). Other strains of *E. coli* which also could serve as suitable hosts include DH1 (ATCC No. 33849) and C600. These strains and the MM294 and RR1 strains are widely commercially available.

In transformation protocols, including those disclosed by Maniatis et al., supra, and Hanahan, supra, only a small portion of the host cells are actually transformed, due to limited plasmid uptake by the cells. The cells that have been transformed can be identified by placing the cell culture on agar plates containing suitable growth medium and a phenotypic identifier, such as an antibiotic. Only those cells that have the proper resistance gene (e.g., to the antibiotic) will survive. If the recombinant pBR322 plasmid is used to transform *E. coli* strain MM294, transformed cells can be identified by using tetracycline as the phenotypic identifier.

Preparation of a Synthetic Oligonucleotide Screening Probe

A radiolabeled synthetic oligonucleotide corresponding to a portion of the known amino acid sequence of human IL-1 is used as a probe to screen the cDNA library. The hybridization of the synthetic oligonucleotide probe with plasmid cDNA prepared from the library clones is subsequently identified by autoradiography.

The N-terminal portion of the amino acid composition of the IL-1 molecule was initially sequenced by applicants and found to be composed of the residues: NH$_2$-Ala-Pro-Val-Arg-Ser-Leu-Asn-Cys-Thr-Leu-Arg-Asp-Ser-Gly-Gln-Lys-Ser-Leu-Val-Met-Ser-Gly-Pro-Tyr-Glu-Leu-Lys-Ala-Leu-His-Leu-Gln-Gly -Gln-Asp-Met-Glu-Gln-Gln-Val, is employed as the basis for the synthetic oligonucleotide probe. This particular portion of the amino acid sequence of IL-1 has the advantage of being short enough to be relatively easily chemically synthesized, while also being long enough to provide sufficient information to be useful in preparing a direct probe for the IL-1 gene. Also, this sequence corresponds to a particular codon composition that is relatively free of ambiguity.

Applicants developed a synthetic oligonucleotide from the above amino acid sequence for use as a probe to screen plasmid DNA thought to contain the IL-1 gene. The probe is composed of the following sequence which corresponds to the antisense sequence coded for by the above amino acid sequence downstream from the Met residue: 5'-AC TTG TTG TTC CAT GTC TTG GCC TTG CAG GTG CAG GGC TTT CAG TTC GTA GGG GCC GGA CAT-3'. This probe has the advantage of being short enough to be easily synthesized, while being long enough to contain sufficient information to be useful as a probe for the IL-1 gene.

Although the described oligonucleotide sequence is a preferred composition of the synthetic probe of the present invention, it is to be understood that probes of other compositions corresponding to other segments of amino acid sequence of the IL-1 molecule can be employed without departing from the spirit or scope of the present invention.

The synthetic oligonucleotide probes may be chemically synthesized by well-known techniques, such as by phosphodiester or triester methods. The details of the triester synthesis technique are set forth in Sood et al., 4 *Nucl. Acid Res.* 2557 (1977); and, Hirose et al., 28 *Tet. Lett.* 2449 (1978). After synthesis, the oligonucleotide probe is labeled with T4 polynucleotide kinase and $^{32}$P-ATP. A standard protocol from the labeling procedure is set forth in Maniatis et al., supra at 122. Advantageously, the oligonucleotide probes can be synthesized with OH 5' termini thereby avoiding the phosphatase procedure typically required.

Screening of cDNA Library

In the screening procedure of the present invention, the transformants are pooled into groups each composed of approximately 2,000 transformants. The replicated plasmids are extracted from the transformants using any one of several well-known techniques, such as by alkaline lysis. Plasmid DNA is prepared by cleaving the plasmids at the Pvu II and Hind III restriction sites, both being unique sites on the hybrid plasmid. The resulting DNA segments are fractionated by electrophoresis on agarose gel and then directly analyzed by Southern blotting as described in Southern, 98 *J. Mol. Biol.* 503 (1975). The DNA that binds to the nitrocellulose filter in the Southern blotting procedure is hybridized with the labeled oligonucleotide probe. The specific DNA fragments that hybridize to the probe are identified by autoradiography.

The particular pool(s) of clones that give a signal following autoradiography are plated out and used in direct bacterial colony hybridization on a nitrocellulose filter with the same above-identified oligonucleotide probes. After completion of the hybridization, the nitrocellulose filter is monitored by autoradiography to identify a positive colony. In the present invention, applicants discovered one such positive colony. Plasmid DNA designated as IL-1 Z-14 is prepared from the particular positive colony identified.

Characterization of Screened cDNA

The plasmid DNA prepared above is characterized by restriction enzyme mapping. Various strategies for restriction enzyme mapping are discussed by Maniatis et al., supra at 374. One standard technique involves the partial digestion of end-labeled fragments of linear DNA. This technique was developed by Smith and Birnstiel, 3 *Nucl. Acids Res.* 2387 (1976). A partial restriction enzyme map of the IL-1 X-14 plasmid in the region of the IL-1 gene is shown in FIG. 1. The distance between restriction sites is given in base pairs 9"bp"). The Pst I restriction sites shown in the brackets are those generated by the cloning procedures.

The mapped plasmid cDNA illustrated in FIG. 1 was sequenced using the chain-termination method. This method of nucleotide sequencing was originated by Sanger et al., 70 *Proc. Natl. Acad. Sci. (USA)* 5463 (1977). See U.S. Pat. No. 4,322,499. Methods for chain-termination sequence determination are set forth in the Amersham Handbook entitled, *M13 Cloning and Sequencing*, Blenheim Cresent, London (1983) (hereinafter "Amersham Handbook"); Messing, 2 *Recombinant DNA Technical Bulletin, NIH Publication No.* 79–99, 2, 43–48 (1979); Norrander et al., 26 *Gene* 101 (1983); Cerretti et al., 11 *Nucl. Acids Res.* 2599 (1983); and, Biggin et al., 80 *Proc. Natl. Acad. Sci. (USA)* 3963 (1983). M13 filamentous phage are employed as vectors to clone the DNA sequences of interest. These phage vectors provide single-stranded DNA templates which are readily sequenced by the chain-termination method, which involves priming a single-stranded template molecule with a short primer strand having a free 3' hydroxyl group and then using DNA polymerase to copy the template strand in a chain extension reaction using all four deoxyribonucleotide triphosphates, i.e., dATP, dCTP, dGTP, and dTTP (collectively referred to as "dNTPs"), with one of them being radiolabeled. In the synthesis reaction, a nucleotide specific chain terminator lacking a 3'-hydroxyl terminus, for instance, a 2',3' dideoxynucleotide triphosphate ("ddNTP"), is used to produce a series of different length chain extensions. The terminator has a normal 5' terminus so that it can be incorporated into a growing DNA chain, but lacks a 3' hydroxyl terminus. Once the terminator has been integrated into the DNA chain, no further deoxynucleotide triphosphates can be added so that growth of the chain stops. Four separate synthesizing reactions are carried out, each having a ddNTP of one of the four nucleotide dNPTs, i.e., dATP, dCTP, dGTP and dTTP. One of the normal dNTPs is radiolabeled so that the synthesized strands after having been sorted by size on a polyacrylamide gel, can be autoradiographed. The chain extensions from the four reactions are placed side by side in separate gel lanes so that the pattern of the fragments from the autoradiography corresponds to the DNA sequence of the cloned DNA.

The DNA and corresponding amino acid sequences of the plasmid cDNA in FIG. 1, as determined by the above techniques, is illustrated in FIG. 2. The nucleotides are numbered from the beginning of the sequence shown in FIG. 2. The amino acids are numbered beginning from the mature $NH_2$-terminus of the IL-1 protein, i.e., the Ala residue, marked with a star, and extending to the Ser residue (No. 153) located adjacent the termination codon TAA. The coding region of the IL-1 gene, extending from the Ala codon to the TAG termination codon, is shown as a box portion in FIG. 1. The restriction enzyme cleaving sites identified in FIG. 1 ar also indicated in FIG. 2.

In preparation for the sequencing procedures, the plasmid cDNA section shown in FIG. 1 is digested with various restriction endonucleases and then the resulting DNA fragments cloned into M13 phage vectors to form single stranded DNA templates. A universal primer is used to sequence upstream and downstream from intermediate locations of the sense and antisense strands. Rather than relying on the sequencing results obtained from sequencing the entire length of the fragments with a single chain termination procedure, additional synthetically produced primers are used to initiate the chain termination procedure from other intermediate locations along the lengths of the strands. By this process, both strands of the plasmid cDNA shown in FIG. 1 are sequenced in overlapping fashion, thereby serving to redundantly confirm the sequences.

It is to be understood that rather than employing the chain-termination technique outlined above, other known methods may be utilized to sequence the IL-1 gene without departing from the spirit or scope of the present invention. For instance, the chemical degradation method of Maxam and Gilbert as set forth in 74 Proc. Nat'l Acad. Sci. (USA) 560 (1977) can be used.

Amino acid sequences studies of IL-1 prepared as above and purified were conducted according to the method of Stern et al., Proc. Natl. Acad. Sci. (USA) 871 (1984). The endopeptidase, cyanogen bromide was used to cleave the IL-1 at the methionine residues and then the resulting fragments analyzed by standard Edman degradation method. By this procedure, applicants have confirmed that the C-terminal of the IL-1 protein is composed of the amino acid sequence: Gln-Phe-Val-Ser-Ser. This establishes that the "natural" IL-1 is not processed by removal of amino acids from this end of the molecule after translation from mRNA. This is important because it is clear that much of the RNA sequence is removed from the N-terminus of the IL-1 gene during the maturation of IL-1 from its precursor.

Expression of Functional IL-1 From cDNA Clone

To determine whether the cDNA coding region of the IL-1 X-14 clone could encode functional IL-1, the clone is expressed in a prokaryotic/eukaryotic host system. A hybrid cDNA fragment containing the coding region of the IL-1 X-14 clone is inserted into a shuttle expression vector having two sets of replication sequences, a first sequence for amplification of the vector in prokaryotic host cells, and a second sequence for high level expression of the foreign structural protein, i.e., IL-1, in eukaryotic host cells. The transformed eukaryotic host cells are harvested and assayed for expression of mature IL-1 by use of the above detailed thymocyte proliferation assay and IL-2 conversion assay.

Various types of shuttle vectors have been developed. A common type includes an origin of replication and promoter sequences that signal DNA replication in prokaryotic cells, typically E. coli and a comparable origin of replication and promoter sequences that signal DNA replication in eukaryotic cells, most commonly yeast cells. The shuttle vector also includes a phenotypic marker, such as a drug resistant gene, for selection of the transformed prokaryotic cells. The shuttle vector has a comparable phenotypic marker change for selection of transformed eukaryotic cells. Ideally, for high level expression of IL-1, all protein coding sequences are removed from the eukaryotic promoter sequence to avoid expression of an undesired protein. Also, to this end, a natural or synthetic initiator codon sequence, i.e., ATG, is attached to the 5' end of the inserted coding region of the IL-1 gene.

A preferable shuttle vector for carrying out the present invention is designated as pY ADH. As illustrated schematically in FIG. 3, the pY ADH plasmid includes an origin of replication (from plasmid pBR322) for high copy DNA expression in E. coli, and an ampicillin ("$Amp^R$") resistant gene for selection of transformed E. coli cells. The shuttle vector also includes the 2u circle origin of replication and a yeast Trp I gene for selection of transformed yeast hosts in yeast (trp minus) trp auxotrophs. The shuttle vector further includes the yeast promoter sequence from the alcohol dehydrogenase gene ("ADH") for propagation of the plasmid in both yeast and E. coli hosts. This promoter sequence is especially advantageous for use in the present invention due to the high level expression of this gene in yeast, and because the complete DNA sequence of this gene is known. All protein coding sequences, including the initiator ATG codon, have been removed from the ADH promoter fragment. The pY ADH shuttle vector includes a number of unique substrate sites for cleavage with restriction enzymes, i.e., Eco RI and Stu I.

Figure 3:
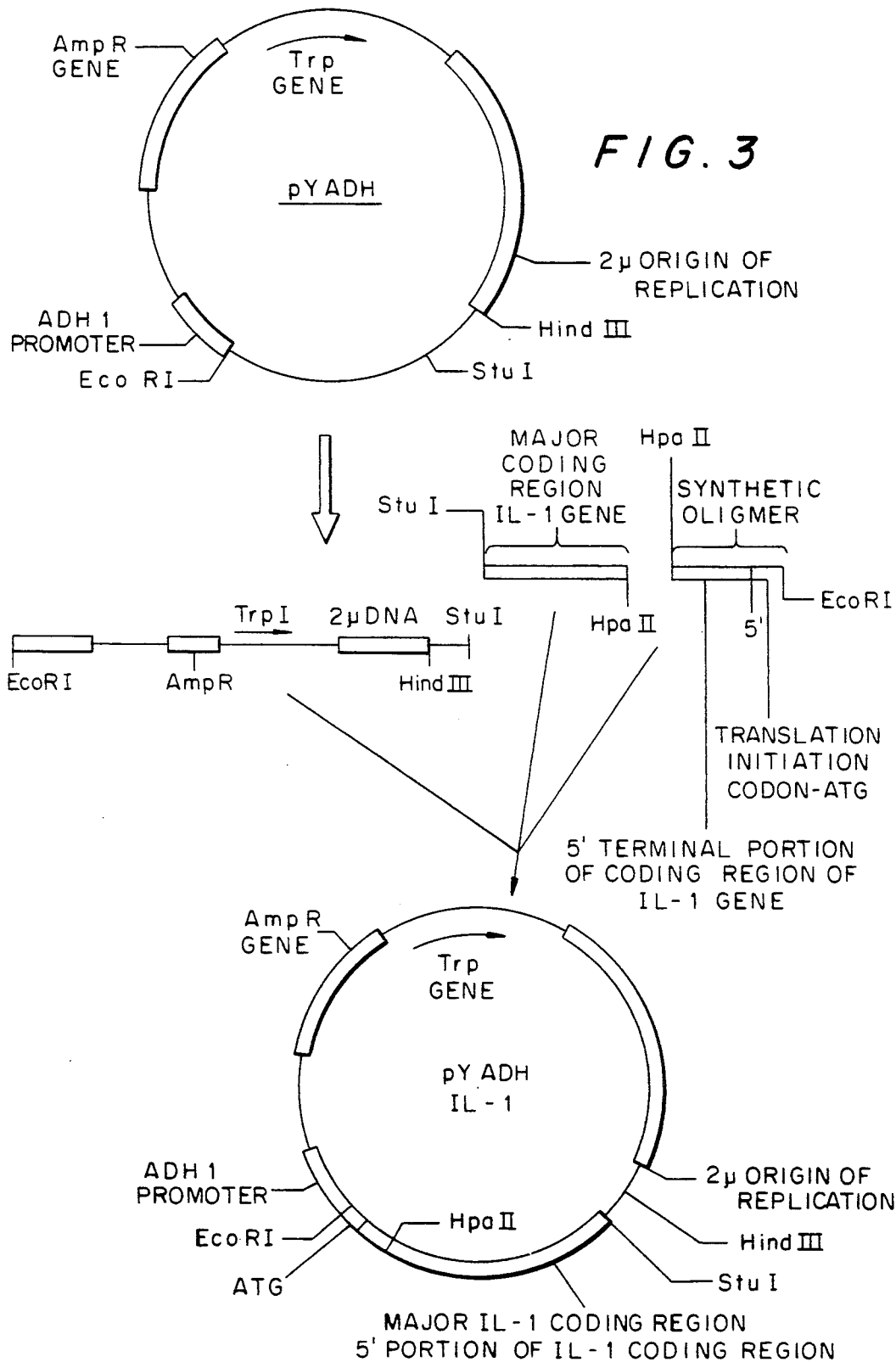

As illustrated in FIG. 3, the pY ADH IL-1 plasmid is prepared as an expression vector for expression of IL-1 gene by insertion of the coding region of the IL-1 gene in plasmid pY ADH. Samples of this shuttle vector are on deposit with the American Type Culture Collection ("ATCC"), 12361 Parklawn Drive, Rockville, Md. 20852, under Accession No. 39967. The coding region of the IL-1 gene is removed from the cDNA plasmid, prepared above. Due to the absence of a unique restriction enzyme cleavage site at precisely the 5' end of the coding region of the IL-1 gene, a major portion of the coding region is cleaved from the plasmid cDNA with the restriction enzymes Hpa II and Pst I. The Hpa II site is located slightly downstream from the 5' end of the gene coding region. Thereafter, a synthetic oligonucleotide containing the cleaved 5' end of the gene is chemically synthesized with a Hpa II cohesive 3' terminal for convenient ligation to the "natural" major IL-1 cDNA fragment. Since, as noted above, all protein coding sequences were removed from the ADH promoter sequence, the synthetic oligonucleotide is synthesized with an ATG initiation codon at its 5' end.

The IL-1 cDNA fragment together with the synthetic oligonucleotide are inserted in shuttle vector pY ADH which previously has been digested with appropriate restriction enzymes corresponding to the configurations of the 5' terminal of the synthetic oligonucleotide and the 3' terminal of the major IL-1 cDNA fragment. The resultant recombinant shuttle vector pY ADH IL-1 is used to transform a prokaryotic host, e.g., *E. coli*, for high copy amplification of the shuttle vector. After this initial transformation process, the recombinant shuttle vector is isolated from the *E. coli* host and then employed to transform a eukaryotic host, e.g., yeast cells for high level expression of IL-1. The transformed yeast hosts are harvested and the resulting supernatant is assayed for biological activity utilizing the above described thymocyte proliferation and/or IL-1 conversion assays.

The processes and products of the present invention are further illustrated by the following examples.

EXAMPLE 1

Preparation of Polyadenylated mRNA

Leukocyte concentrates of a volume of 350–400 ml, obtained from human whole blood (mixture from Portland, Ore. Red Cross), were mixed with and diluted in $Ca^{++}$, $Mg^{++}$ free phosphate buffered saline ("PBS") layered onto Histopaque (Sigma Chemical Company, St. Louis, Mo.) and then centrifuged at $600 \times g$ for 30 minutes at room temperature. The interface layer, consisting of the leukocytes, was recovered, washed with PBS and centrifuged at $400 \times g$ for 10 minutes at room temperature. The cells were washed two more times in $Ca^{++}$, $Mg^{++}$ free PBS and centrifuged at $200 \times g$ for 10 minutes after each washing.

Cells were then added to plastic culture flasks in Roswell Park Memorial Institute ("RPMI")-1640 medium together with 10% fetal bovine serum (v/v). Following a two-hour incubation at 37° C., nonadherent cells were decanted and the flasks were then replenished with additional serum supplemented RPMI-1640 medium containing 20 ug/ml *E. coli* LPS at 20 ug/ml. Sixteen hours later, adherent LPS stimulated cells were harvested for RNA.

Total RNA was extracted from the adherent mononuclear cells by the method as described by Chirgwin et al., supra. In this procedure guanidinium thiocyanate was used to denature the cellular protein including the RNase at a rate that exceeds the rate of RNA hydrolysis by RNase. The mRNA was removed from the cellular protein by ultracentrifugation through a dense cushion of cesium chloride.

Thereafter, polyadenylated mRNA was separated from the extracted protein on an oligo (dT)-cellulose chromatography column using the method disclosed by Maniatis et al., supra at 197. Briefly, the column was prepared with application buffer composed of 20 mM Tris-Cl (pH 7.6), 0.5M NaCl, 1 mM ethylene diamine tetraacetate ("ETDA") and 0.1% sodium dodecyl sulfate ("SDS"). The protein pellet was dissolved in water and application buffer and then loaded onto the column. The nonadsorbed material was eluted by initial washings with application buffer followed by additional washings with application buffer containing 0.1M NaCl. The retained polyadenylated mRNA was eluted with buffers of reduced ionic strength composed of 10 mM Tris-Cl (pH 7.5), 1 mM EDTA and 0.05% SDS. The eluted polyadenylated mRNA was precipitated at −20° C. with 1/10 volume sodium acetate (3M, pH 5.2) and 2.2 volumes of ethanol. After elution of the polyadenylated mRNA from the oligo (dT)-cellulose column, the integrity of the polyadenylated mRNA was confirmed by electrophoresis through agarose gels as detailed in Maniatis et al., supra at 199.

The polyadenylated mRNA was sized by electrophoresis through methylmercury agarose. Gel fractions corresponding to different size classes of mRNA were then translated in vitro, either by use of rabbit reticulocyte lysates or by injection in frog *X. laevis* oocytes as described above. Fluids liberated by either reticulocyte translations or by mRNA injected oocytes were then tested for the presence of IL-1 activity using the assays set forth above. mRNA gel fractions which, when translated in vitro gave rise to IL-1 activity, were selected as a source of mRNA for cDNA construction.

EXAMPLE 2

Construction of cDNA Library

A library of double-stranded cDNA corresponding to the mRNA was prepared from the purified mRNA in Example 1 by employing the standard procedure detailed by Maniatis et al., supra at 229. Oligo-dT was hybridized to the polyadenylated tail of the mRNA to serve as the primer for the reverse transcription of the first cDNA strand. The enzyme avian myeloblastosis virus ("AMV") reverse transcriptase synthesized the first DNA strand by using the mRNA as a template. This procedure resulted in a hairpin loop being formed at the 3′ end of the initial cDNA strand that served as an integral primer for the second cDNA strand. After the mRNA strand had been degraded with NaOH, the second cDNA strand was synthesized with DNA polymerase I. The hairpin was then removed with nuclease S1 to produce double-stranded cDNA molecules.

The double-stranded cDNA was fractionated into size classes by Sephacryl S-400 (Pharmacia Fine Chemicals) column chromatography and monitored by analysis using alkaline agarose electrophoresis employing end-labeled fragments of pBR322 DNA as molecular-weight markers. DNA strands having a length of less than 500 bp were culled out to avoid needles cloning of these undersized cDNA fractions.

The double-stranded cDNA fractions, as prepared above, were inserted into the Pst I site of the pBR322 plasmid (Pharmacia Fine Chemicals) by the method disclosed by Maniatis et al., supra, beginning at 239. In this procedure the double-stranded cDNA was tailed with poly (dC) at its 3′ ends. The plasmid pBR322 was digested with Pst I endonuclease and then tailed with poly (dG) at its 3′ ends. The tailed plasmid DNA and the tailed cDNA were annealed with annealing buffer (0.1M NaCl, 10 mM Tris-Cl (pH 7.8) and 10 mM ETDA) to form novel recombinant plasmids. All restriction enzymes described herein are commercially available from New England Biolabs, Beverly, Mass.

The recombinant plasmids were transformed into *E. coli* strain MM294 by using the procedure of Hanahan, supra in which the *E. coli* cells were prepared by growth in elevated levels of $Mg^{2+}$. The transformation hosts were plated and then transformants were identified by use of tetracycline as a phenotypic identifier. By use of this technique, applicants obtained approximately $2 \times 10^6$ independent transformants.

EXAMPLE 3

Preparation of Synthetic Oligonucleotide Screening Probes

A synthetic oligonucleotide was employed as a probe in screening the cDNA library prepared as set forth above in Example 2. The probe was composed of the following composition: 5′ AC TTG TTG TTC CAT GTC TTG GCC TTG CAG GTG CAG GGC TTT CAG TTC GTA GGG GCC GGA CAT 3'. The oligonucleotide probe was chemically synthesized by triester method as detailed by Sood et al., supra and Hirose et al., supra.

After chemical synthesis has been completed, the 5' ends of the oligonucleotide probes were labeled with $^{32}P$. To facilitate labeling, the 5' ends of the oligonucleotide were synthesized with OH termini, thereby eliminating the phosphatase treatment which typically must be employed when labeling DNA fragments. The labeling protocol included adding 1 ul of the synthetic oligonucleotides to 16 ul of $^{32}P$ - ATP (3000 ci/mM), 1 microliter ("ul") (10 U) of T4 polynucleotide kinase and 2 ul of 10×kinase buffer I. The 10×kinase buffer I was composed of 0.5M Tris-Cl (pH 7.6), 0.1M $MgCl_2$, 50 mM dithiothreitol, 1 mM spermidine and 1 mM ETDA. The reaction was carried out at 37° C. for 30 minutes, and thereafter the synthesized oligonucleotides were extracted with phenol/chloroform. The labeled probes were separated from unlabeled oligonucleotides by chromatography on or centrifugation through Sephadex G-50 columns (Pharmacia Fine Chemicals).

EXAMPLE 4

Screening of cDNA Library

To facilitate initial screening of the cDNA library prepared in Example 2 above, the transformed bacteria cultures were pooled into groups each having approximately 2,000 transformants of different clones. Plasmid DNA was removed from samples of the host bacteria by standard alkaline lysis method detailed by Ish-Horowicz and Burke, 9 *Nucl. Acids Res.* 2989 (1981). The isolated plasmids were separated into two fragments. This was accomplished by initially digesting the plasmids to completion with Pvu II and Hind III. To this end, the plasmids were redissolved in 20 ul of 1×Hind III buffer (7 mM Tris, (pH 7.4), 7 mM magnesium chloride, 60 mM NaCl) and then 1 ul of Pvu II and 1 ul of Hind III restriction endonucleases are added. This mixture was incubated at 37° C. for two hours.

Next, the plasmid digests were fractionated by electrophoresis through 0.8% agarose gel with markers of appropriate size. The agarose gel was blotted onto nitrocellulose filter using the standard method described by Southern, supra. After the transfer process, the filter was air dried and baked for two hours at approximately 80° C. under a vacuum to bind the DNA fragments to the nitrocellulose.

The bound DNA was next hybridized with the labeled oligonucleotide probes. Briefly, the baked nitrocellulose was presoaked in 6×saline sodium citrate ("SSC") (20 X SSC is composed of 175.3 g of NaCl and 88.2 g of sodium citrate in 800 ml of $H_2O$, with pH adjusted to 7.0 with 10N NaOH) and then incubated at 50° C. for 2–4 hours in prehybridization buffer composed of 6×SSC, 0.5% NP40 detergent, 0.1% sarcosyl, 5×Denhardt's solution (0.02% Ficoll, 0.02% polyvinyl pyrrolidone, 0.02% BSA) and 100 ug/ml denatured salmon sperm DNA (Sigma Type III, sodium salt). The filter was then incubated overnight at 50° C. with the $^{32}P$-labeled oligonucleotide probe ($10^6$ cpm/ug) (from Example 3) in hybridizing solution as above. After overnight hybridization, the filter was washed extensively with 6×SSC at room temperature and then for 5 minutes at 50° C. with 6×SSC. After air drying, the filter was subjected to autoradiography at −70° C.

From the autoradiography, applicants found several hybridizing bands. The pool of clones from which the plasmid DNA that produced the hybridizing bands was plated out and then used in direct bacterial colony hybridization on nitrocellulose paper with the labeled oligonucleotide probe under the same hybridizing conditions as above. By this process, a single positive colony was identified.

EXAMPLE 5

Restriction Enzyme Mapping of Screened cDNA

Plasmid, designated as IL-1 X-14, was prepared from the identified positive colony by the procedures set forth in Example 4. Samples of the IL-1 X-14 plasmid transformed into *E. coli* strain RR1 are on deposit with the ATCC under Accession No. 39925. Thereafter, the IL-1 X-14 plasmid was analyzed by restriction enzyme mapping using the technique developed by Smith and Birnstiel, supra, involving partial digestion of end-labeled fragments of the linearized DNA. The DNA fragments were labeled at their 5' termini with $^{32}P$-phosphoryl groups using polynucleotide kinase and $^{32}P$ - ATP. The labeled DNA strands were then cleaved asymmetrically with a suitable restriction enzyme to provide two fragments, each labeled at only one of its ends. These labeled fragments were isolated by gel electrophoresis. Each of the two fragments was partially digested by appropriate restriction enzymes. Although a large spectrum of digestion fragments may be produced, the labeled fragments form a simple overlapping series each having a common labeled terminus. These fragments were fractionated by gel electrophoresis and then examined by autoradiography. The locations of the fragments on the gel correspond directly to the order of the restriction sites along the plasmid DNA.

By this procedure, applicants have partially mapped the restriction sites, as shown in FIG. 1, of the IL-1 X-14 plasmid in the region of the IL-1 gene. The numbers shown between the restriction sites of the gene correspond to the approximate distances between the sites, in base pairs.

EXAMPLE 6

Sequencing of Screened cDNA

The DNA segment shown in FIG. 1 was sequenced by the dideoxy chain-termination method essentially as described in the Amersham Handbook supra, with the variations set forth below. The DNA segment was digested with Hind III and Pst I restriction endonucleases and then the resulting DNA fragments were cloned into strains mp18 and mp19 of the M13 single-stranded filamentous phage vector (Amersham, Arlington Heights, Ill.). The mp18 and mp19 phage vectors, as set forth in Norrander et al. supra, contain the following unique cloning sites: Hind III; Sph I; Pst I; Sal I; Acc I; Hinc II; Xba I; BamHI; Xma I; Sma I; Kpn I; Sst I; and, EcoRI. The composition of the mp18 and mp19 vectors are identical, with the exception that the order of the above-identified restriction sites are reversed in the mp19 vector so that both strands of a DNA segment may be conveniently sequenced with the two vectors. The mp18 mp19 vectors, with fragments of the cDNA segment of FIG. 1 inserted therein, were used to transform *E. coli* MJ103 and JM105 of the strain K12 (Bethesda Research Laboratories, Bethesda, Md.) to produce replicate single-stranded DNA templates containing single-stranded inserts of the sense and antisense strands.

The synthetic universal primer: 5'-CCCAGTCAC-GACGTT-3' (P-L Biochemicals, Milwaukee, Wis.), was annealed to the single-strand DNA templates and used to prime DNA synthesis upstream and downstream from a location between nucleotides 476 and 477 (FIG. 2) as described above at page 16. Thereafter, the extension fragments were size-separated by gel electrophoresis and autoradiographed from which the nucleotide sequences of the fragments were deduced. Three additional primers were employed to prime synthesis from intermediate locations along the sense strands of the DNA segment in FIG. 2. A primer having the composition: 5'-CTGGAGAGTGTAGATCC-3', corresponding to nucleotides 671 through 688 (FIG. 2), was used to prime synthesis of the sense strand in the downstream direction from nucleotide No. 688. The composition of this primer strand was established from the sequencing information previously obtained by use of the universal primer. A second synthetic primer of the composition: 5'-GATATAACTGACTTCAC-3' (corresponding to nucleotides 851 through 868 in FIG. 2) was used in sequencing the sense strand in the downstream direction from nucleotide No. 868. A third primer having the sequence: 5'-GATTCGTAGCTGGATGC-3' (corresponding to nucleotides No. 235 through No. 218) was employed to sequence the antisense strand in the upstream direction from nucleotide No. 218.

By the above "walk down" method, both strands of the plasmid cDNA in FIG. 1 were sequenced in an overlapping, redundant manner thereby confirming their nucleotide sequence. It is to be understood that other synthetic primers could have been employed to initiate chain extensions from other locations along the strands without departing from the scope of the present invention. The above primer strands were chemically synthesized by triester method as detailed by Sood et al., supra and Hirose et al., supra. It is to be understood, however, that other well-known techniques, such as by phosphodiester method, may be employed to synthesize the primer strands.

Deoxyadenosine 5' (alpha-[$^{35}$S] thio) triphosphate (hereinafter "dATP [alpha-$^{35}$S]") was used as the radioactive label in the dideoxy sequencing reactions. Also, rather than using the gel set forth at page 36 of the Amersham Handbook, a 6% polyacrylamide gel was employed (6% polyacrylamide gel, 0.4 mm thick, containing 7 M, urea 100 mM Tris borate (pH 8.1), and 2 mM EDTA).

As noted above, the nucleotide sequence of the plasmid DNA in FIG. 1 is illustrated in FIG. 2. This segment of DNA was found to include the region of the IL-1 gene coding for mature IL-1. The nucleotides are numbered from the beginning of the DNA segment in FIG. 2. The corresponding amino acids, as determined by the nucleotide sequence and by protein sequence analysis, are set forth above the appropriate codons. The amino acid composition of the IL-1 gene extends from the mature NH$_2$-terminus of the IL-1 molecule, i.e., the Ala residue, in IFG. 2 (from which the numbering of the amino acid residues begins), to the Ser residue (No. 153) immediately preceding the termination codon TAA. Various restriction enzyme cleaving sites are also indicated in FIG. 2. The coding region of the IL-1 gene in FIG. 2 is illustrated as a boxed section in FIG. 1.

Amino acid sequence studies of IL-1 were conducted according to the method of Stern et al., supra, wherein cyanogen bromide was employed to cleave the IL-1 at the methionine residues. The resulting fragments were separated by size by standard ion-exchange methods. The isolated peptide fragments were then sequenced by automated amino terminal Edman degradation using an Applied Biosystems Model 470 protein sequencer. By this process, applicants have confirmed the results obtained by nucleotide sequencing that the C-terminal of the IL-1 protein is composed of the amino acid sequence: Gln-Phe-Val-Ser-Ser. This establishes that the "natural" IL-1 is not processed by removal of amino acids from this end of the molecule after translation from mRNA. This is significant since from the nucleotide sequence of the IL-1 gene in FIG. 2, it is clear that a significant amount of RNA sequence is removed from the N-terminus of the IL-1 gene during the maturation of IL-1 from its precursors.

EXAMPLE 7

Expression of Mature IL-1

The coding region of the IL-1 gene was removed from the cDNA clone of FIG. 1 and then inserted into the pY ADH shuttle vector to form the recombinant expression plasmid pY ADH IL-1. The restructuring scheme for preparing the pY ADH IL-1 shuttle expression vector is shown in FIG. 3. This plasmid was amplified in *E. coli* host cells and then employed to transform yeast host cells for high level expression of mature IL-1. The functionality of the expressed IL-1 was confirmed by using the thymocyte proliferation and IL-2 conversion assays, detailed above.

A major portion of the coding region of the IL-1 gene from the Hpa II site (base #457 in FIG. 2) to the 3' flanking region of the gene was removed from the cDNA plasmid segment illustrated in FIGS. 1 and 2 by use of the Hpa II and Pst I restriction enzymes in the standard protocol set forth in Maniatis et al., supra at 104. The IL-1 gene segment was cleaved from the cDNA clone at the Hpa II site, which is located 29 nucleotides downstream from the 5' end of the gene, because no convenient restriction site was found to correspond precisely with the 5' terminal of gene. The 3'-Pst I site of the excised IL-1 gene segment was filled in with T4 DNA polymerase to create a blunt end compatible with the Stu I site of the shuttle vector, discussed below.

A synthetic oligonucleotide was chemically synthesized to add back the 5' terminal portion of the coding region of the IL-1 gene and also to create a translation initiation codon at the 5' end of the coding region. The composition of the oligonucleotide, as shown in Table 1 below, includes an Eco RI cohesive 5' terminal followed by an ATG initiation codon and then the 5' end of the coding region of the IL-1 gene (to the Hpa II site). Although the oligonucleotide shown in Table I was chemically synthesized by triester technique as detailed by Sood et al., supra and Hirose et al., supra, it is to be understood that the oligonucleotide can be prepared by other methods, such as by phosphodiester method.

TABLE 1

| ECO R1 | Met | Ala | Pro | Val | Arg | Ser | Leu | Asn | Cys | Thr | Leu |
|---|---|---|---|---|---|---|---|---|---|---|---|
| 5'-AATTCAAC | ATG | GCA | CCT | GTA | CGA | TCA | CTG | AAC | TGC | ACG | CCT -3' |
| GTTG | TAC | CGT | GGA | CAT | GCT | AGT | GAC | TTG | ACG | TGC | GAGGC |
| | | | | | | | | | | | Hpa II |

Also, rather than cleaving the coding region of the IL-1 gene at the Hpa II site, the plasmid cDNA in FIG. 2 could be cleaved at a restriction enzyme site in the 5' flanking region of the gene. Thereafter, the nucleotides of the flanking region can be sequentially removed by standard techniques.

The pY ADH shuttle vector was prepared for ligation to the synthetic oligonucleotide and the excised major portion of the coding region of the IL-1 gene by digestion of the vector to completion with the restriction endonucleases Eco RI and Stu I by standard techniques, as set forth in Maniatis et al., supra at 104. The desired larger fragment from the digestion of the pY ADH plasmid was isolated by electrophoresis on 0.7% agarose gel at 100 volts at 22° C. for two hours.

As shown in FIG. 3, the synthetic DNA oligomer, the excised major portion of the coding region of the IL-1 gene and the desired linearized pY ADH fragment were ligated together in a reaction mixture composed of 100 ug of the pY ADH vector fragment (Eco RI - Stu I), 40 ug of the major IL-1 cDNA fragment (Hpa II, Pst I [blunt]), 5 ug of synthetic oligonucleotide (Eco R I - Hpa II), 1 ug of T4 DNA ligase and sufficient T4 ligase buffer (0.4M Tris [pH 7.4]0.1 MgCl$_2$, 0.1M dithiothreitol, 10 mM spermidine, 10 mM ATP and 1 mg/ml BSA) to form a 20 ul reaction volume. The reaction was carried out by incubation at 15° C. for 15 hours.

The resulting recombinant plasmid, designated as pY ADH IL-1, was then transformed into E. coli strain RR1 using standard transformation techniques, such as set forth in Bolivar et al., supra and Peacock et al., supra. The host cells were cultured to amplify the pY ADH IL-1 plasmid, and then the plasmids were removed from the host bacteria by standard alkaline method as detailed by Maniatis et al., supra at 368 and by Ish-Horowicz and Burke, supra. The plasmid DNA was purified by centrifugation to equilibrium in cesium chloride-ethidium bromide density gradients, as set forth in Maniatis et al., supra at 93. It is to be understood that other techniques for extracting/concentrating the amplified plasmid DNA from the E. coli may be employed without departing from the scope or spirit of the present invention.

The amplified pY ADH IL-1 plasmid, as prepared above, was then employed to transform the protease deficient yeast strain 20B-12 (alpha, pep 4.3, Trp 1) of S. Cerevisiae by standard techniques. Prior to transformation, the 20B-12 strain was grown in culture in YP-glucose medium (200 ml) to cultures of $2 \times 10^7$ cells/ml. The cells were harvested by centrifugation at 1000×g for 5 minutes at 22° C., and then the resulting pellet washed with sterile distilled water.

The yeast cells were then concentrated by resuspending in 20 ml of SED (1M sorbitol, 25 mM ETDA [pH 8.0], and 50 mM dithiothreitol) and incubated for 10 minutes at 30° C. The cell-buffer mixture was then centrifuged for 5 minutes at 300×g. The pellet was washed once with 200 ml of 1M sorbitol and the cells resuspended in 20 ml of SCC (1M sorbitol, 0.1M sodium citrate [pH 5.8], 0.1M ETDA). Glusulase, to break down the cell walls, in an amount of 0.2 ml was added to the solution and then the solution incubated at 30° C. for 30 minutes with occasional gentle shaking.

The presence of spheroplast was assayed by diluting 10 ul of yeast cells into a drop of 5% sodium dodecyl sulfate (SDS) (wt./vol.) on a microscope slide to observe for "ghosts" at 400×phase contrast.

The cell mixture was then centrifuged at 300×g for 3 minutes. The resulting pellet was twice washed with 20 ml of 1M sorbitol. The pellet was then washed once with STC (1M sorbitol, 10 mM, CaCl, 10M Tris HCl [pH 7.5]).

The yeast spheroplasts were then transformed with the previously prepared plasmid vector in a procedure adapted from Beggs, 275 Nature (London) 104 (1978). The pelleted protoplasts are suspended in 1.0 ul of STC and then divided into 100 ml aliquots in 10 ul disposable tubes (Falcon #2059). Then, from 1 to 10 ul of the DNA plasmids were added to each aliquot (0.5 to 5 ug). The mixture was rested at room temperature for 10 minutes and then 1 ml of PEG (20% PEG 4000, 10 mM CaCl$_2$, 10 mM Tris - HCl [pH 7.4]) was added to each aliquot to promote DNA uptake. After 10 minutes at room temperature, the mixture was centrifuged for 5 minutes at 350×g. The resulting pellet was resuspended in 150 ul of SOS (10 ml of 2M sorbitol, 6.7 ul of YEP [0.13 ml of 1M of CaCl, 27 ul of 1% leucine, and 3.7 ml of H$_2$O]). This mixture was incubated for 20 minutes at 30° C.

Thereafter the protoplast/DNA mixture was plated in the presence of yeast minimal medium containing 1.2M sorbitol and 3% agar at 45° C. and without tryptophan. The minimal medium was composed of 0.67 Difco yeast, Nitrogen Base, 0.5% casamino acids, 2% glucose. By maintaining the protoplast/DNA mixture in this medium, only transformants survived, i.e., those that contained the Trp 1 gene.

Prior to biological assay, the transformants were inoculated from the minimal medium into rich medium (1% yeast extract, 2% peptone, 2% glucose) and grown at 30° C. for 15-20 hours until the late exponential phase. At the time of harvest, the protease inhibitor phenyl methyl sulfonyl fluoride (PMSF) was added to 1 mM. The culture was then centrifuged at 400×g to pellet the cells. Thereafter, the cells were washed once in 0.1 vol. cold H$_2$O. For breakage, the cells were resuspended in 0.01 vol. cold H$_2$O containing 1 mM PMSF and vortexed with glass beads (¼ vol.) for 2 minutes. The cell debris and glass beads were pelleted by centrifugation. The resulting supernatant was found to exhibit IL-1 activity. This was ascertained by utilizing the supernate in both of the thymocyte proliferation and IL-1 conversion assays, discussed above.

As will be apparent to those skilled in the art in which the invention is addressed, the present invention may be embodied in forms other than those specifically disclosed above without departing from the spirit or essential characteristics of the invention. The particular embodiments of the present invention, described above, are therefore to be considered in all respects as illustrative and not restrictive. The scope of the present invention is as set forth in the appended claims rather then being limited to the examples contained in the foregoing description.

The embodiments of the invention in which an exclusive property or privilege is claimed are defined as follows:

1. An isolated, double-stranded DNA molecule comprising a DNA sequence encoding a translation product that displays human IL-1 β activity in the thymocyte proliferation assay wherein one strand of said molecule hybridizes to an oligonucleotide probe after overnight hybridization at about 50° C. in 6×SSC solution and washing a room temperature with 6×SSC solution followed by washing at 50° C. in 6×SSC, and wherein
    (1) said probe comprises the nucleotide sequence: ACTTGTTGTTCCATGTCTTGGCCTTGCAGGTGCAGGGCTTTCAGTTCGTAGGGGCCGGACAT; and
    (2) said translation product is approximately the 153 c-terminal amino acid residues of the amino acid sequence set forth in FIG. 2.

2. An isolated DNA molecule according to claim 1, wherein said molecule is a cDNA molecule.

3. An isolated DNA molecule according to claim 1, wherein said DNA sequence comprises nucleotides No. 428 through No. 886 of FIG. 2.

4. An isolated DNA molecule according to claim 1, wherein said translation product consists of amino acid residues No. 1 through No. 153 in FIG. 2 and, optionally, an N-terminal methionine residue.

5. An isolated DNA molecule according to claim 1, wherein said molecule is a recombinant plasmid.

6. An isolated DNA molecule according to claim 5, wherein said recombinant plasmid is an expression plasmid capable of directing the translation of said polypeptide in a yeast cell.

7. A yeast cell transformed by an expression vector according to claim 6.

8. A yeast cell transformed by a recombinant plasmid according to claim 3.

9. A yeast cell according to claim 8, wherein said yeast cell is a *S. cerevisiae* cell.

10. A method for producing a polypeptide having biological activity in a thymocyte proliferation assay, said polypeptide consisting of amino acid residues No. 1 through No. 153 in FIG. 2 and, optionally, an N-terminal methionine residue, comprising the steps of
    (A) growing a recombinant yeast host cell according to claim 7 under conditions favorable for expression and recovery of said polypeptide; and
    (B) recovering said polypeptide.

11. A method according to claim 10, wherein said yeast cell is a *Saccharomyces cerevisiae* cell.

* * * * *